(12) United States Patent
Mao et al.

(10) Patent No.: US 12,377,188 B2
(45) Date of Patent: Aug. 5, 2025

(54) DOUBLE-CROSSLINKED FIBRIN GEL, RAW MATERIAL COMPOSITION AND KIT THEREOF, AND APPLICATION THEREOF

(71) Applicant: ZHEJIANG UNIVERSITY, Zhejiang (CN)

(72) Inventors: Zhengwei Mao, Zhejiang (CN); Lisha Yu, Zhejiang (CN); Weilin Wang, Zhejiang (CN); Yuan Ding, Zhejiang (CN)

(73) Assignee: ZHEJIANG UNIVERSITY, Zhejiang (CN)

( * ) Notice: Subject to any disclaimer, the term of this patent is extended or adjusted under 35 U.S.C. 154(b) by 0 days.

(21) Appl. No.: 18/841,788

(22) PCT Filed: Aug. 17, 2023

(86) PCT No.: PCT/CN2023/113503
§ 371 (c)(1),
(2) Date: Aug. 27, 2024

(87) PCT Pub. No.: WO2024/078129
PCT Pub. Date: Apr. 18, 2024

(65) Prior Publication Data
US 2025/0108143 A1    Apr. 3, 2025

(30) Foreign Application Priority Data
Oct. 12, 2022  (CN) .......................... 202211244546.2
Oct. 12, 2022  (CN) .......................... 202211249717.0

(51) Int. Cl.
A61L 24/10   (2006.01)
A61L 24/00   (2006.01)
A61L 24/02   (2006.01)
A61L 24/04   (2006.01)
A61L 24/08   (2006.01)

(52) U.S. Cl.
CPC ......... A61L 24/106 (2013.01); A61L 24/0031 (2013.01); A61L 24/02 (2013.01); A61L 24/046 (2013.01); A61L 24/08 (2013.01)

(58) Field of Classification Search
None
See application file for complete search history.

(56) References Cited

U.S. PATENT DOCUMENTS

| 6,162,241 | A | 12/2000 | Coury et al. | |
|---|---|---|---|---|
| 2014/0205636 | A1* | 7/2014 | Khatri | A61L 24/0094 424/94.64 |
| 2015/0166735 | A1 | 6/2015 | Bidault et al. | |
| 2016/0022862 | A1 | 1/2016 | Alsberg | |
| 2017/0173209 | A1 | 6/2017 | Russo | |

FOREIGN PATENT DOCUMENTS

| CN | 108699517 A | 10/2018 |
|---|---|---|
| CN | 110240712 A | 9/2019 |
| CN | 110743041 A | 2/2020 |
| CN | 114392387 A | 4/2022 |
| CN | 115671372 A | 2/2023 |
| CN | 115920118 A | 4/2023 |
| KR | 20200037936 A | 4/2020 |
| WO | 2020231191 A1 | 11/2020 |
| WO | 2021237543 A1 | 12/2021 |

OTHER PUBLICATIONS

Assmann, A., et al. Biomaterials 140: 115 -127 (2017). (Year: 2017).*
Fares, M., et al., Biomater. Sci. 24: 2938-2950 (2018). (Year: 2018).*
International Search Report (with English translation) and Written Opinion issued in PCT/CN2023/113503, dated Dec. 5, 2023, 15 pages provided.
Office Action issued in Chinese Application No. 202211244546.2, dated Mar. 13, 2023, with English translation.
Office Action issued in Chinese Application No. 202211249717.0, dated May 30, 2023, with English translation.
Notice of Allowance issued in Chinese Application No. 202211244546. 2, dated May 29, 2023, with English translation.
Notice of Allowance issued in Chinese Application No. 202211249717. 0, dated Jun. 14, 2023, with English translation.
Zhu et al., "Biomimetic microenvironment constructed from gelatin methacrylamide/platelet-rich plasma hydrogel promotes the function of insulinoma cell line MIN6 in mice", China Journal Electronic Publishing House, Apr. 2023, vol. 27; Issue 12; pp. 1824-1831, with English Abstract.

(Continued)

Primary Examiner — David J Blanchard
Assistant Examiner — Daniel F Coughlin
(74) Attorney, Agent, or Firm — HSML P.C.

(57) ABSTRACT

The present invention provides a double-crosslinked fibrin gel, which is a solid hydrogel composed of a network structure with a blocking function and a network structure with an adhesion function, where the network structure with the blocking function is a three-dimensional fibrin network, and the network structure with the adhesion function is a three-dimensional photosensitive gel network; each channel of the photosensitive gel network has a group of the fibrin network inside, and each group of the fibrin network has overall continuity; on the whole, the three-dimensional fibrin network disperses disorderly throughout a surface and an interior of the solid hydrogel. The present invention further provides a raw material composition, a kit for preparing the double-crosslinked fibrin gel, and an application of the kit to prepare an in-situ rapid clotting and hemostatic material. The double-crosslinked fibrin gel prepared by the kit has a fast and efficient hemostatic effect, also can be widely applied for hemostasis of accidental trauma or a surgical wound.

22 Claims, 1 Drawing Sheet

(56) References Cited

OTHER PUBLICATIONS

Yuan, "Construction and Evaluation of Sodium Alginate Based Hydrogels for Tissue Repair Application", Donghua University, PhD Dissertation, 2017, with English Abstract, 139 pages.

Chang et al., "An Injectable Hybrid Gelatin Methacryloyl (GelMA)/Phenyl Isothiocyanate-Modified Gelatin (Gel-Phe) Bioadhesive for Oral/Dental Hemostasis Applications", Polymers 2021, 13, 2386. https://doi.org/10.3390/polym13142386.

Zhang et al., "Hyaluronic acid-fibrin interpenetrating double network hydrogel prepared in situ by orthogonal disulfide cross-linking reaction for biomedical applications", ScienceDirect, Acta Biomaterialia 38 Available online Apr. 28, 2016 pp. 23-32.

\* cited by examiner

DOUBLE-CROSSLINKED FIBRIN GEL, RAW MATERIAL COMPOSITION AND KIT THEREOF, AND APPLICATION THEREOF

TECHNICAL FIELD

The present invention belongs to the field of biomedical materials, and in particular to a double-crosslinked fibrin gel for hemostasis of accidental trauma or surgical bleeding, and an application method thereof.

BACKGROUND

Uncontrollable bleeding occurring after trauma or during surgery is the leading cause of death worldwide, resulting in over 2 million deaths annually. Uncontrolled bleeding in surgical and traumatic environments often leads to complications and adverse outcomes. Therefore, controlling bleeding volume is an important measure to reduce complications and mortality, and improve the prognosis of patients.

At present, some local hemostatic materials have been developed to assist in controlling bleeding during surgery. Commonly used surgical sealants on the market include fibrin glue and synthetic tissue adhesives. Fibrin glue is the most widely used hemostatic agent with good biocompatibility, which can assist in hemostasis in various surgical procedures, simulate coagulation cascade reactions, form fibrin clots in situ at the bleeding site, and block bleeding. However, the adhesion strength of fibrin glue decreases due to the influence of sustained tissue tension and blood, making fibrin glue easily washed away by blood flow, which is not conducive to its hemostatic performance, and the hemostatic effect of fibrin glue is limited by its poor adhesion to wet tissue. On the other hand, synthetic tissue adhesives such as cyanoacrylate adhesives, despite having good adhesion ability, are limited in their application due to their high cytotoxicity and difficulty in removal.

In order to break through the current bottleneck of low adhesion of biological adhesives applied to wet tissue surfaces, there are studies using methacryloylated gelatin as a hemostatic gel material in the prior art. This kind of double-bond modified gelatin is obtained by functionalizing the free amino group of gelatin into a methacrylamide group through methacrylic anhydride. Under the light condition of a specific wavelength, the photoinitiator in the material absorbs light energy to produce free radicals, thereby bonding methacryloylated gelatin molecules to form a solid-phase gel. Methacryloylated gelatin has good biocompatibility, as well as good mechanical properties and adhesion. However, methacryloylated gelatin does not have a procoagulant function, which limits its hemostatic ability to a certain extent; the photocuring time of methacryloylated gelatin is 5-10 seconds, which is long, and methacryloylated gelatin is easily washed away by blood flow during the photocuring process; and in severe bleeding, a large amount of blood weakens its adhesion ability. To compensate for this deficiency, a study of Luo et al. introduced hemocoagulase with a coagulation function into methacryloylated gelatin, and the constructed hemostatic gel had an improved hemostatic effect (Guo Y, Wang Y, Zhao X, et al. Snake extract-laden hemostatic bioadhesive gel cross-linked by visible light. Sci Adv. 2021. 7(29)). However, the methacryloylated gelatin carrying hemagglutinase constructed in this study could only contact the blood with a very small amount of hemagglutinase on the surface of the gel, and the concentration of fibrinogen in the blood was low (2-4 g/L), and the formed fibrin crosslinking was not enough to block the wound; and at the same time, before the completion of photocuring of methacryloylated gelatin, its wound blocking effect was weak, which greatly limits its hemostatic effect. Wang et al. constructed a thrombin-methacryloylated gelatin hydrogel for multi-stage healing of diabetic wounds in 2020. By incorporating free thrombin and thrombin-loaded liposomes into methacryloylated gelatin, the initial release of thrombin was achieved to promote hemostasis and continuous release of thrombin to regulate late healing of diabetic wounds (Chongyang W, Tianyi W, Guangwang L, et al. Promoting coagulation and activating SMAD3 phosphorylation in wound healing via a dual-release thrombin-hydrogel. Chemical Engineering Journal. 2020. 397(C)). The disadvantage of this study in constructing gel is similar to that of Luo et al., gel releases less thrombin, and has less contact with fibrinogen in the blood, so it cannot form fibrin crosslinking, which reduces the hemostatic effect due to the weak blocking effect on the wound.

In addition, there were reports in the prior art that other photocuring materials are used to prepare hemostatic materials. For example, Chinese patent literature CN 111116973 A disclosed a polyvinyl alcohol hemostatic porous material with an active hemostasis function. By adding polymers with an active hemostatic function such as chitosan or (and) thrombin to the sponge obtained by photocatalytic cross-linking of modified polyvinyl alcohol, the sponge is endowed with active hemostatic effect. However, the hemostasis time reported in this paper was 90 s-100 s, which was long, inevitably leading to a poor hemostatic effect. This was because 1) the pre-formed sponge could not fully contact with wet tissue, resulting in a worse blocking effect than the in-situ formed gel; 2) in a dry state, thrombin in the sponge was not easy to free, thus limiting its procoagulant function; 3) the concentration of fibrinogen in the blood was low (2-4 g/L), and the fibrin crosslinking formed is not enough to block the wound. Therefore, it was difficult to meet the needs of rapid hemostasis when there was a large amount of bleeding during surgery; and in the face of bleeding from wounds on visceral organs or body surfaces, the effect of its expansion and compression on the wound was limited, which weakens the hemostatic effect to a certain extent; at the same time, when the sponge was removed, it could cause secondary damage to the wound because of its adhesion to the hemostatic site.

The ideal hemostatic material should not rely on the coagulation mechanism of the body, and can even play a hemostatic role when the body has coagulation disorders. At the same time, it has a good wet tissue adhesion ability and an ideal clotting and hemostatic speed. Therefore, it is particularly important to invent a novel hemostatic material that can solve the problems of poor wet tissue adhesion and limited hemostatic effects of existing hemostatic materials.

SUMMARY

In order to overcome the above shortcomings in the prior art, the primary purpose of the present invention is to provide an adhesive that can rapidly stop bleeding, quickly achieve gelation, and has high adhesion, so as to achieve the effects of procoagulation and strong adhesion at the same time.

Another purpose of the present invention is to provide a raw material composition and a kit that can be used to prepare the adhesive, in order to facilitate the clinical promotion and application of the adhesive.

Further another purpose of the present invention is to provide a method of hemostasis using the kit.

In order to achieve the above purposes, the present invention adopts the following technical solutions:

In the first aspect, the present invention provides a double-crosslinked fibrin gel, which is a solid hydrogel composed of a network structure with a blocking function and a network structure with an adhesion function; the network structure with the blocking function is formed prior to the network structure with the adhesion function. The network structure with the blocking function is a three-dimensional fibrin network, and the network structure with the adhesion function is a three-dimensional photosensitive gel network; each channel of the photosensitive gel network has a group of the fibrin network inside, and each group of the fibrin network has overall continuity; on the whole, the three-dimensional fibrin network disperses disorderly throughout a surface and an interior of the solid hydrogel.

In the double-crosslinked fibrin gel of the present invention, the three-dimensional fibrin network as a scaffold can play the role of enhancing the strength of the gel, and its formation process is used to convert the fibrinogen in the blood into fibrin, thus playing the role of initially blocking the wound. With the increase of a fibrin ratio, the gelation time of the solid hydrogel will be shortened, tissue adhesion will be reduced, but the pores of the gel will be enlarged, and the procoagulation function will be increased. The three-dimensional photosensitive gel network plays the role of providing the strength and tissue adhesion of the gel. With the increase of the proportion of the photosensitive gel network in the solid hydrogel, the tissue adhesion of the solid hydrogel is also increased, but the gelation time is also prolonged, the pores of the gel are decreased, and the procoagulant function is reduced. In view of the different effects of the above two networks on the overall hemostatic performance of the gel, the present invention further optimizes the proportion of the two networks in the gel through experiments. In a preferred double-crosslinked fibrin gel, the volume ratio of the three-dimensional fibrin network to the three-dimensional photosensitive gel network is 0.5-3; preferably 0.5-2; and most preferably 1. Under these optimal volume ratios, the two networks can bring better hemostatic performance to the gel as a whole, especially when the volume ratio of the fibrin network to the photosensitive gel network reaches 1:1, the hemostatic performance of the gel can reach the best, i.e., to achieve rapid procoagulation while improving the strength and adhesion of gel.

In the double-crosslinked fibrin gel of the present invention, the photosensitive gel can be formed by photocrosslinking of multiple existing photocurable high molecular materials (i.e., photosensitive materials), and the photosensitive material can be a methacryloylated high molecular polymer or a derivative thereof, a polyacrylate high molecular polymer or a derivative thereof, or a high molecular composite system including the both.

Furthermore, the methacryloylated high molecular polymer or the derivative thereof above can be selected from any one or a mixture of two or more of: methacryloylated gelatin or a derivative thereof, methacryloylated hyaluronic acid or a derivative thereof, methacryloylated sodium alginate or a derivative thereof, methacryloylated silk fibroin or a derivative thereof, methacryloylated chitosan or a derivative thereof, and methacryloylated carboxymethyl chitosan or a derivative thereof. The polyacrylate high molecular polymer or the derivative thereof above can be selected from polyether diacrylate or a derivative thereof, or polyethylene glycol diacrylate or a derivative thereof. A most preferred photosensitive material of the present invention is methacryloylated gelatin or a derivative thereof, or methacryloylated silk fibroin or a derivative thereof.

Furthermore, the derivative of the methacryloylated high molecular polymer above include a polymer after modification of one or more functional groups thereof. A modifiable functional group of the methacryloylated gelatin includes any one or two or more of amino, carboxyl, sulfydryl, hydroxyl, or guanidyl; the derivative of methacryloylated hyaluronic acid includes a polymer after modification of one or more functional groups thereof, where a modifiable functional group includes any one or two or more of hydroxyl, carboxyl, acetylamino, or hydroxymethyl; the derivative of methacryloylated sodium alginate includes a polymer after modification of one or more functional groups thereof, where a modifiable functional group includes any one or two of carboxyl and hydroxyl; the derivative of methacryloylated silk fibroin includes a polymer after modification of one or more functional groups thereof, where a modifiable functional group includes any one or two or more of amino, carboxyl, sulfydryl, hydroxyl, or guanidyl; the derivative of methacryloylated chitosan includes a polymer after modification of one or more functional groups thereof or a polymer after multiple chemical reactions, where a modifiable functional group includes any one or two of amino or hydroxyl, and multiple chemical reactions that can occur any one or two or more of alkylation, acylation, carboxymethylation, hydrolysis, oxidation, and reduction chemical reactions.

A molecular weight range of the methacryloylated high molecular polymer or the derivative thereof above is 5-400 kDa, while a molecular weight range of the polyacrylate high molecular polymer or the derivative thereof above is 700-1000 kDa.

Furthermore, the high composite molecular system including the methacryloylated high molecular polymer or the derivative thereof above includes: any one or two or more of a methacryloylated gelatin-polyvinyl alcohol system, a methacryloylated gelatin-polyurethane system, a methacryloylated gelatin-polylactic acid system, a methacryloylated gelatin-cellulose system, a methacryloylated hyaluronic acid-polyvinyl alcohol system, a methacryloylated hyaluronic acid-polyurethane system, a methacryloylated hyaluronic acid-polylactic acid system, a methacryloylated hyaluronic acid-cellulose system, a methacryloylated sodium alginate-polyvinyl alcohol system, a methacryloylated sodium alginate-polyurethane system, a methacryloylated sodium alginate-polylactic acid system, a methacryloylated sodium alginate-cellulose system, a methacryloylated silk fibroin-polyvinyl alcohol system, a methacryloylated silk fibroin-polyurethane system, a methacryloylated silk fibroin-polylactic acid system, a methacryloylated silk fibroin-cellulose system, a methacryloylated chitosan-polyvinyl alcohol system, a methacryloylated chitosan-polyurethane system, a methacryloylated chitosan-polylactic acid system, a methacryloylated chitosan-cellulose system, a methacryloylated carboxymethyl chitosan-polyvinyl alcohol system, a methacryloylated carboxymethyl chitosan-polyurethane system, a methacryloylated carboxymethyl chitosan-polylactic acid system, and a methacryloylated carboxymethyl chitosan-cellulose system.

In the double-crosslinked fibrin gel of the present invention, the fibrin network can be formed from fibrinogen by enzymatic crosslinking. The fibrinogen can be any one of human fibrinogen, bovine fibrinogen, or porcine fibrinogen.

In the second aspect, the present invention provides a raw material composition for preparing the double-crosslinked fibrin adhesive according to the first aspect of the present invention, including composition A and composition B, where the composition A includes 10-200 parts of a photosensitive material, 1-3 parts of a photoinitiator, 0.14-0.28 parts of an enzyme, and 1.11-8.88 parts of a water-soluble inorganic calcium salt, and the composition B includes 5-100 parts of the photosensitive material, 1-2 parts of the photoinitiator, and 30-50 parts of the fibrinogen in parts by weight; and a mass ratio of the composition A to the composition B is 1.4:10-14:1; preferably 1.4:1-1.4:10; more preferably 1.4:1-1.4:5; and most preferably 1.4:1.

In a preferred solution of the present invention, parts by weight of the photosensitive material in the composition A are greater than parts by weight of the photosensitive material in the composition B. The parts by weight of the photosensitive material in the composition A and the composition B is conducive to an enzymatic reaction between the enzyme in the composition A and the fibrinogen in the composition B, forming a stable fibrin network structure.

In the raw material composition of the present invention, the fibrinogen can form a fibrin network through an enzymatic crosslinking reaction under action of the enzyme, and the photosensitive material can form a photosensitive gel through a photocrosslinking reaction under action of the photoinitiator. Therefore, after mixing the composition A and the composition B in the raw material composition of the present invention according to the mass ratio, a double-crosslinked fibrin adhesive can be prepared by illumination. The adhesive is a solid hydrogel, and there will be both a three-dimensional fibrin network and a three-dimensional photosensitive gel network in its structure; each channel of the photosensitive gel network has a group of the fibrin network inside, and each group of the fibrin network has overall continuity; and on the whole, the three-dimensional fibrin network disperses disorderly throughout a surface and an interior of the solid hydrogel. When this solid hydrogel is formed on a bleeding wound site, a fibrin clot can be formed on the surface of the wound instantly (about 1 s), which plays a preliminary role in blocking the wound and blocks the outflow of blood; at the same time, the enzyme in the fibrin clot converts the fibrinogen in the blood into a clot, which has an efficient procoagulant function; furthermore, under light excitation, the photosensitive material can form a photocured gel within 5-10 s; and the photocured gel has strong adhesion, which can resist the impact of blood flow and protect the crosslinking of fibrin from being washed away by blood. In a word, in the raw material composition of the present invention, the composition A and the composition B can first instantly form the fibrin network to play a scaffold role after mixing, and the photosensitive gel will also be rapidly formed later, and the photosensitive gel formed later is wrapped on the fibers in the fibrin network.

The present invention finds through experiments that the mass ratio of the composition A to the composition B in the raw material composition is related to the initial wound blocking effect and adhesion strength of the double-crosslinked fibrin adhesive: when the mass ratio of the composition A to the composition B is in the range of 1.4:10-1.4:1, as a ratio of the composition A increases, the procoagulant function of the double-crosslinked fibrin adhesive is improved, the initial wound blocking effect is increased, and the adhesion strength is increased; and when the mass ratio of the composition A to the composition B is in the range of 1.4:1-14:1, as the ratio of the composition A increases, the procoagulant function, initial wound blocking effect, and adhesion strength of the double-crosslinked fibrin adhesive are not further increased. This means that when the mass ratio of the composition A to the composition B is 1.4:1, the best hemostatic effect can be obtained and the optimal material utilization rate can be achieved. At this ratio, the volume ratio of the two networks generated by crosslinking can reach about 1:1, which can bring the optimal procoagulant function and adhesion strength to the prepared gel.

In a preferred raw material composition of the present invention, the composition A includes 80-200 parts of the photosensitive material, 1-3 parts of the photoinitiator, 0.14-0.28 parts of the enzyme, and 1.11-8.88 parts of the water-soluble inorganic calcium salt, and the composition B includes 30-100 parts of the photosensitive material, 1-2 parts of the photoinitiator and 30-50 parts of the fibrinogen in parts by weight.

In a more preferred raw material composition of the present invention, the composition A includes 100-200 parts of the photosensitive material, 1-3 parts of the photoinitiator, 0.14-0.28 parts of the enzyme, and 1.11-8.88 parts of the water-soluble inorganic calcium salt, and the composition B includes 30-50 parts of the photosensitive material, 1-2 parts of the photoinitiator and 30-50 parts of the fibrinogen in parts by weight.

In a most preferred raw material composition of the present invention, the composition A includes 100-150 parts of the photosensitive material, 1-3 parts of the photoinitiator, 0.14-0.28 parts of the enzyme, and 1.11-8.88 parts of the water-soluble inorganic calcium salt, and the composition B includes 30-50 parts of the photosensitive material, 1-2 parts of the photoinitiator and 30-50 parts of the fibrinogen in parts by weight.

In the third aspect, the present invention also provides a method of preparing the raw material composition, including: preparing a mixed solution of a photosensitive material and a photoinitiator dissolved in a solvent, mixing the mixed solution with a solution containing thrombin and a calcium ion to obtain a first precursor solution, and controlling a concentration ratio of the photosensitive material, the photoinitiator, the enzyme, and the calcium ion in the first precursor solution to be 10-200:1-3:0.14-0.28:1.11-8.88; and mixing the mixed solution with a solution containing fibrinogen to obtain a second precursor solution, and controlling a concentration ratio of the photosensitive material, the photoinitiator and the fibrinogen in the second precursor solution to be 5-100:1-2:30-50; thus, a liquid raw material composition including the first precursor solution and the second precursor solution can be obtained; and the liquid raw material composition can also be further processed according to a conventional method to obtain a solid raw material composition, such as a freeze-dried powder, a sponge or a granule.

In the preparation method of the present invention, in order to maintain the activity of the photosensitive material in the first precursor solution, the first precursor solution is controlled to be placed in a room temperature environment for less than 30 minutes.

In the preparation method of the invention, in order to give consideration to the uniformity of fibrinogen dispersion and the speed of photocrosslinking of the photosensitive material, a concentration of the photosensitive material in the first precursor solution is preferably controlled to be greater than 0.5% (w/v), and a concentration of the photosensitive material in the second precursor solution is lower than the concentration of the photosensitive material in the first precursor solution. Therefore, the fibrinogen solution is more easily uniformly dispersed in the second precursor solution with a relatively low concentration of the photosensitive material, and can quickly and fully contact the enzyme after the two precursor solutions are mixed, and complete enzyme crosslinking occurs instantly to form a uniformly distributed fibrin network; at the same time, a higher concentration of the photosensitive material in the first precursor solution can increase an overall concentration of the photosensitive material after the two precursor solutions are mixed, making it achieve an ideal concentration required for gelation, which is conducive to shortening photocrosslinking time and increasing the adhesion and strength of gel.

In the preparation method of the present invention, when the first precursor solution and the second precursor solution are prepared, a temperature of the mixed solution is preferably controlled not to be higher than 37° C.

A further preferred method of preparing the raw material composition injection specifically includes the following steps:
1) preparing a first mixed solution of the photosensitive material and the photoinitiator dissolved in the solvent, and controlling a concentration ratio of the photosensitive material and the photoinitiator to be 10-200:1-3 and a concentration of the photosensitive material to be 0.5%-30% (w/v);
2) preparing a second mixed solution of the photosensitive material and the photoinitiator dissolved in the solvent, and controlling a concentration ratio of the photosensitive material and the photoinitiator to be 5-100:1-2 and a concentration of the photosensitive material to be lower than that in the first mixed solution in 1);
3) mixing the first mixed solution prepared in 1) with the solution containing the enzyme and the calcium ion to obtain the first precursor solution, and controlling the concentration ratio of the photosensitive material, the photoinitiator, the enzyme, and the calcium ion to be 10-200:1-3:0.14-0.28:1.11-8.88; and
4) mixing the second mixed solution prepared in 2) with the solution containing the fibrinogen to obtain the second precursor solution, and controlling the concentration ratio of the photosensitive material, the photoinitiator and the fibrinogen to be 5-100:1-2:30-50.

In the preparation method of the present invention, the solution containing the enzyme and the calcium ion is preferably prepared according to a method of: adding a solvent and a water-soluble inorganic calcium salt solution to the enzyme, completely dissolving to obtain an enzyme solution containing $Ca^{2+}$, and controlling enzyme activity to be 500 IU-2000 IU/ml and a $Ca^{2+}$ concentration to be 60-100 mmol/L in the obtained solution.

In the preparation method of the present invention, a concentration of the fibrinogen in the solution containing the fibrinogen is preferably 5%-10% (w/v).

In the preferred preparation method of the present invention, the concentration of the photosensitive material in the first precursor solution is controlled at 1%-30% (w/v), further preferably at 8%-30% (w/v), and more preferably at 10%-20%.

In the preferred preparation method of the present invention, the enzyme activity in the first precursor solution is controlled to be not less than 200 IU/ml, preferably not less than 500 IU/ml; and more preferably not less than 1000 IU/ml.

In the preferred preparation method of the present invention, the calcium ion concentration in the first precursor solution is controlled to be not less than 20 mmol/L, preferably not less than 30 mmol/L, and more preferably not less than 40 mmol/L.

In the preferred preparation method of the present invention, the concentration of the photosensitive material in the second precursor solution is controlled to be not less than 0.5% (w/v) and not higher than the concentration of the photosensitive material in the first precursor solution, further preferably not less than 1% (w/v) and not higher than the concentration of the photosensitive material in the first precursor solution, and more preferably 1%-10% (w/v) and not higher than the concentration of the photosensitive material in the first precursor solution.

In the preferred preparation method of the present invention, the concentration of the fibrinogen in the second precursor solution is controlled to be not less than 3% (w/v), and more preferably 3%-5% (w/v).

In the fourth aspect, the present invention also provides a kit of preparing the double-crosslinked fibrin gel according to the first aspect of the present invention, including a first precursor reagent and a second precursor reagent packaged independently of each other, where the first precursor reagent includes 10-200 parts of a photosensitive material, 1-3 parts of a photoinitiator, 0.14-0.28 parts of an enzyme, and 3.33-5.55 parts of a water-soluble inorganic calcium salt, and the second precursor reagent includes 5-100 parts of the photosensitive material, 1-2 parts of the photoinitiator and 30-50 parts of fibrinogen in parts by weight; a mass ratio of the first precursor reagent to the second precursor reagent is 1.4:10-14:1; preferably 1.4:1-1.4:10; more preferably 1.4:1-1.4:5; and most preferably 1.4:1.

In a preferred kit of the present invention, the first precursor reagent contains 80-200 parts of the photosensitive material, 1-3 parts of the photoinitiator, 0.14-0.28 parts of the enzyme, and 3.33-5.55 parts of the water-soluble inorganic calcium salt, and the second precursor reagent contains 30-100 parts of the photosensitive material, 1-2 parts of the photoinitiator and 30-50 parts of the fibrinogen in parts by weight.

In a more preferred kit of the present invention, the first precursor reagent contains 100-200 parts of the photosensitive material, 1-3 parts of the photoinitiator, 0.14-0.28 parts of the enzyme, and 3.33-5.55 parts of the water-soluble inorganic calcium salt, and the second precursor reagent contains 30-50 parts of the photosensitive material, 1-2 parts of the photoinitiator and 30-50 parts of the fibrinogen in parts by weight.

In a most preferred kit of the present invention, the first precursor reagent contains 100-150 parts of the photosensitive material, 1-3 parts of the photoinitiator, 0.14-0.28 parts of the enzyme, and 3.33-5.55 parts of the water-soluble inorganic calcium salt, and the second precursor reagent contains 30-50 parts of the photosensitive material, 1-2 parts of the photoinitiator and 30-50 parts of the fibrinogen in parts by weight.

In the kit of the present invention, the photosensitive materials contained in the first precursor reagent and the second precursor reagent are photosensitive biohydrogel materials, which can be multiple existing photocurable polymer materials; and the photoinitiators contained in the first precursor reagent and the second precursor reagent are substances that can generate free radicals after absorbing light energy under a light condition of a specific wavelength. The photoinitiator can generate free radicals after absorbing light energy, which can bond the photosensitive material molecules, thus quickly forming a solid-phase gel. An ideal photosensitive material should have good biocompatibility and biodegradability, as well as good mechanical and adhesive properties.

In the raw material composition or the kit of the present invention, the photosensitive material can be a methacryloylated high molecular polymer or a derivative thereof, a polyacrylate high molecular polymer or a derivative thereof, or a high molecular composite system including the both.

Furthermore, the methacryloylated high molecular polymer or the derivative thereof above can be selected from any one or a mixture of two or more of: methacryloylated gelatin or a derivative thereof, methacryloylated hyaluronic acid or a derivative thereof, methacryloylated sodium alginate or a derivative thereof, methacryloylated silk fibroin or a derivative thereof, methacryloylated chitosan or a derivative thereof, and methacryloylated carboxymethyl chitosan or a derivative thereof. The polyacrylate high molecular polymer or the derivative thereof above can be selected from polyether diacrylate or a derivative thereof, or polyethylene glycol diacrylate or a derivative thereof. A most preferred photosensitive material of the present invention is methacryloylated gelatin or a derivative thereof, or methacryloylated silk fibroin or a derivative thereof.

Furthermore, the derivative of the methacryloylated high molecular polymer above include a polymer after modification of one or more functional groups thereof. A modifiable functional group of the methacryloylated gelatin includes any one or two or more of amino, carboxyl, sulfydryl, hydroxyl, or guanidyl; the derivative of methacryloylated hyaluronic acid includes a polymer after modification of one or more functional groups thereof, where a modifiable functional group includes any one or two or more of hydroxyl, carboxyl, acetylamino, or hydroxymethyl; the derivative of methacryloylated sodium alginate includes a polymer after modification of one or more functional groups thereof, where a modifiable functional group includes any one or two of carboxyl and hydroxyl; the derivative of methacryloylated silk fibroin includes a polymer after modification of one or more functional groups thereof, where a modifiable functional group includes any one or two or more of amino, carboxyl, sulfydryl, hydroxyl, or guanidyl; the derivative of methacryloylated chitosan includes a polymer after modification of one or more functional groups thereof or a polymer after multiple chemical reactions, where a modifiable functional group includes any one or two of amino or hydroxyl, and multiple chemical reactions that can occur any one or two or more of alkylation, acylation, carboxymethylation, hydrolysis, oxidation, and reduction chemical reactions.

A molecular weight range of the methacryloylated high molecular polymer or the derivative thereof above is 5-400 kDa, while a molecular weight range of the polyacrylate high molecular polymer or the derivative thereof above is 700-1000 kDa.

Furthermore, the high molecular composite system including the methacryloylated high molecular polymer or the derivative thereof above includes: any one or two or more of a methacryloylated gelatin-polyvinyl alcohol system, a methacryloylated gelatin-polyurethane system, a methacryloylated gelatin-polylactic acid system, a methacryloylated gelatin-cellulose system, a methacryloylated hyaluronic acid-polyvinyl alcohol system, a methacryloylated hyaluronic acid-polyurethane system, a methacryloylated hyaluronic acid-polylactic acid system, a methacryloylated hyaluronic acid-cellulose system, a methacryloylated sodium alginate-polyvinyl alcohol system, a methacryloylated sodium alginate-polyurethane system, a methacryloylated sodium alginate-polylactic acid system, a methacryloylated sodium alginate-cellulose system, a methacryloylated silk fibroin-polyvinyl alcohol system, a methacryloylated silk fibroin-polyurethane system, a methacryloylated silk fibroin-polylactic acid system, a methacryloylated silk fibroin-cellulose system, a methacryloylated chitosan-polyvinyl alcohol a methacryloylated system, chitosan-polyurethane system, a methacryloylated chitosan-polylactic acid system, a methacryloylated chitosan-cellulose system, methacryloylated carboxymethyl chitosan-polyvinyl alcohol system, a methacryloylated carboxymethyl chitosan-polyurethane system, a methacryloylated carboxymethyl chitosan-polylactic acid system, and a methacryloylated carboxymethyl chitosan-cellulose system.

In a preferred raw material composition or kit of the present invention, the photoinitiator can be selected from a composition of any one or two or more of: lithium phenyl (2,4,6-trimethylbenzoyl)phosphinate, 2-hydroxyl-4'-(2-hydroxyethoxy)-2-methylpropiophenone, ethyl (2,4,6-trimethylbenzoyl)phenylphosphinate, 2-methyl-1-[4-methylthiophenyl]-2-morpholino-1-propanone, methyl ortho-benzoylbenzoate, 2-Benzyl-2-(dimethylamino)-4'-morpholinobutyrophenone, or 2,2-azo (2-methyl-N-(2-hydroxylethyl) propionamide); and most preferably lithium phenyl(2,4,6-trimethylbenzoyl)phosphinate.

In a preferred raw material composition or kit of the present invention, the enzyme can be selected from any one of human thrombin, recombinant human thrombin, bovine thrombin, porcine thrombin, or hemocoagulase.

In a preferred raw material composition or kit of the present invention, the fibrinogen can be selected from any one of human fibrinogen, bovine fibrinogen or porcine thrombin.

In a preferred raw material composition or kit of the present invention, the water-soluble inorganic calcium salt can be selected from calcium chloride, calcium nitrate or calcium sulfate; and most preferably calcium chloride.

In a preferred kit of the present invention, the first precursor reagent and/or the second precursor reagent further include adjuvants and/or additives. The adjuvant is selected from one or two or more of glycine, arginine hydrochloride, sodium citrate, sucrose, and sodium chloride. The additive is selected from one or two or more of growth factors, interleukins, vitamins, and silver ions. The growth factor can be further selected from one or more of a platelet growth factor, an epidermal growth factor or a fibroblast growth factor; the interleukin can be further selected from one or more of interleukin 2, interleukin 6 or interleukin 8; and the vitamin can be further selected from one or more of vitamin B, vitamin C, vitamin E, or vitamin K.

In the kit of the present invention, the first precursor reagent and/or the second precursor reagent can be multiple specific dosage forms that are pharmaceutically or clinically acceptable, and can be a freeze-dried powder, a sponge or a granule.

The kit of the present invention can further include an independently packaged solvent for preparation, where the solvent for preparation is a mixture of any one or more of phosphate-buffered saline solution, HEPES biological buffer solution, 0.9% sodium chloride solution, calcium chloride solution, and deionized water. A preferred dosage form for the solvent for preparation is an injection.

The kit of the present invention can further include an instruction for explaining a method of using the kit.

In the fifth aspect, the present invention also provides a method of rapidly stopping bleeding in situ in a bleeding wound by using the kit according to the fourth aspect of the present invention, including: preparing the first precursor reagent and the second precursor reagent into respective injectable solutions by the solvent for preparation, then injecting or spraying the solutions evenly on a bleeding wound site at the same time, and then irradiating with light at a wave band of 290-480 nm for 10-60 s, which can rapidly form a solid hydrogel in situ at the bleeding wound site.

The bleeding wound includes bleeding of an organ caused by accidental trauma or occurring during surgery; and the organ is a liver, a spleen, a kidney, a stomach and intestine, a heart, or skin.

In the application of the present invention, when the kit is injected into the bleeding wound, (1) a fibrin clot can be formed on the surface of the wound instantly (about 1 second), which plays a preliminary role in blocking the wound, blocks the outflow of blood, and thus compensates for the weak blocking effect of the photosensitive material before the completion of photocuring; (2) at the same time, the enzyme in the fibrin clot converts the fibrinogen in the blood into a clot, which has an efficient procoagulant function; and (3) furthermore, the photosensitive material forms a photocured gel within 5-10 s under light excitation; and the photocured gel has strong adhesion, which can resist the impact of blood flow and protect the crosslinking of fibrin from being washed away by blood. Therefore, the double-crosslinked fibrin gel can be prepared by using the kit or the kit in situ of the present invention, strong adhesion to photocrosslinking can occur at the moment of crosslinking with fibrin, and the double-crosslinked fibrin gel with a fibrin crosslinked network and photocrosslinked network structure is obtained.

Compared with the prior art, the present invention has the advantages of rapid gelation, a fast curing speed, strong wet tissue adhesion, and a good hemostatic effect:

(1) the double-crosslinked fibrin gel kit of the present invention can produce fibrin crosslinking immediately (about 1 s) after mixing, which plays a preliminary blocking role and blocks a blood flow impact.

(2) the enzyme in the double-crosslinked fibrin gel kit of the present invention can convert the fibrinogen in the blood into fibrin crosslinking, which has an efficient procoagulant ability.

(3) the double-crosslinked fibrin gel kit of the present invention can undergo a photocrosslinking reaction in 5-10 seconds to form a photocured gel under the excitation of ultraviolet light or visible light, which provides strong wet tissue adhesion and can protect fibrin crosslinking from being washed away by blood flow.

It is precise because the double-crosslinked fibrin gel provided by the present invention has a good procoagulant function, curing speed, wet tissue adhesion, and rapid hemostatic effect that it can be used for hemostatic applications of liver, spleen, kidney, heart, stomach, and intestine, and skin bleeding in accidental trauma or surgery.

DETAILED DESCRIPTION OF EMBODIMENTS

The following provides a detailed description of the technical problems to be solved, technical solutions, and beneficial effects in the present invention in conjunction with specific embodiments. The following embodiments will assist those skilled in the art in further understanding the present invention, but do not limit the present invention in any form. It should be noted that for those of ordinary skill in the art, several modifications and improvements can be made without departing from the concept of the present invention. These all fall within the scope of protection of the present invention.

Figure 3:
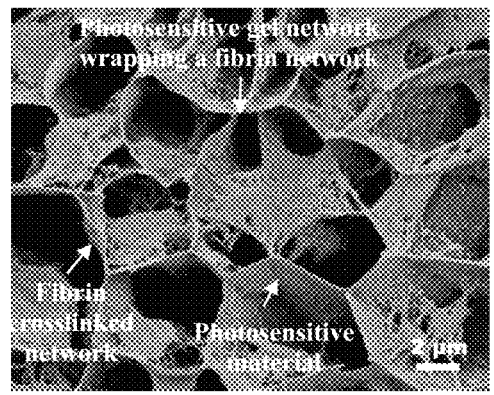
FIG. 3 is an SEM diagram of a double-crosslinked fibrin gel of Example 1.

The present invention provides a double-crosslinked fibrin gel, which is a solid hydrogel composed of a three-dimensional photosensitive gel network and a three-dimensional fibrin network; its microstructure is shown in FIG. 3, with both a fibrin-crosslinked network structure and a photosensitive material-crosslinked porous structure; each channel of the porous structure has a group of the fibrin network, and each group of the fibrin network has overall continuity; on the whole, the three-dimensional fibrin network disperses disorderly throughout a surface and an interior of the solid hydrogel; and the fibrin network structure plays a scaffolding role in the photosensitive gel network channel, and the pore wall of the photosensitive gel porous structure surrounds the fibrin network structure.

The double-crosslinked fibrin gel is prepared according to a method of:

(1) preparation of a composition A solution: adding an enzyme solution containing a calcium ion to a mixed solution dissolved with a photosensitive material and a photoinitiator, and mixing evenly to obtain the composition A solution, which includes the photosensitive material, the photoinitiator and the enzyme; controlling a concentration of the photosensitive material in the obtained composition A solution to be not less than 1% (w/v), preferably not less than 3% (w/v), and more preferably 3%-20% (w/v); and at the same time, controlling enzyme activity to be not less than 200 IU/mL, preferably not less than 500 IU/mL, and more preferably not less than 1000 IU/mL.

(2) preparation of a composition B solution: adding a fibrinogen solution to the mixed solution dissolved with the photosensitive material and the photoinitiator, and mixing evenly to obtain the composition B solution, which includes the photosensitive material, the photoinitiator and the fibrinogen. A concentration of the photosensitive material in the obtained composition B solution is controlled to be not less than 0.5% (w/v), and preferably 1%-10% (w/v); and at the same time, a concentration of the fibrinogen is controlled to be not less than 3% (w/v), and preferably 3%-5% (w/v).

(3) storage method: freeze-drying the obtained composition A solution and composition B solution each in a volume ratio of 1:10-10:1, and storing after forming a spongy shape.

(4) preparation of a double-crosslinked fibrin gel using the above freeze-dried sponge: dissolving a spongy component A and a spongy component B in a solvent to obtain an injectable solution-like component A and component B. The solid hydrogel can be formed quickly in situ by injecting/spraying the equal volumes of a component A solution and a component B solution evenly on a bleeding site and irradiating with blue light or ultraviolet light for 10-60 s. As a preferred solution, the injection tool for the injectable solution during use is a duplex syringe, a syringe, and a Pasteur pipette.

In the preparation scheme, the solvent can be selected from any one or a combination of phosphate-buffered saline solution, HEPES biological buffer solution, 0.9% sodium chloride solution, calcium chloride solution, and deionized water, and the usage amount thereof is not particularly limited, and the solvent can be prepared according to the actually required concentration.

Based on the above implementations, the present invention further lists the following examples for explanation.

Example 1

A preparation method of a double-crosslinked fibrin gel in this example included the following steps:
(1) preparation of a precursor solution of methacryloylated gelatin-lithium phenyl(2,4,6-trimethylbenzoyl)phosphinate: adding the required volume of a 0.9% sodium chloride solution to the powdered lithium phenyl(2,4,6-trimethylbenzoyl)phosphinate, and heating and dissolving in a water bath to obtain two concentrations of lithium phenyl(2,4,6-trimethylbenzoyl)phosphinate solutions: 0.25% (w/v), 0.5% (w/v); taking the required weight of solid methacryloylated gelatin, adding the required concentration of the lithium phenyl(2,4,6-trimethylbenzoyl)phosphinate solution to it, and heating and dissolving in a water bath to obtain two weight in volume percents (w/v) of the methacryloylated gelatin-lithium phenyl(2,4,6-trimethylbenzoyl)phosphinate precursor solutions: 26% (w/v) methacryloylated gelatin-0.5% (w/v) lithium phenyl(2,4,6-trimethylbenzoyl)phosphinate, 10% (w/v) methacryloylated gelatin-0.25% (w/v) lithium phenyl(2,4,6-trimethylbenzoyl)phosphinate;
(2) preparation of a thrombin solution: injecting the required volume and concentration of a calcium chloride solution into thrombin, and completely dissolving to obtain the thrombin solution with thrombin activity of 2000 IU/mL, where a $Ca^{2+}$ concentration was 80 mmol/L;
(3) preparation of a fibrinogen solution: taking the required weight of fibrinogen, slowly placing it in a preheated 0.9% sodium chloride solution, and completely dissolving to obtain the fibrinogen solution with a weight in volume percent (w/v) of 10% (w/v).
(4) preparation of a component A solution: adding the thrombin solution obtained in step (2) to the 26% (w/v) methacryloylated gelatin-0.5% (w/v) lithium phenyl(2,4,6-trimethylbenzoyl)phosphinate precursor solution obtained in step (1), and mixing evenly to obtain the component A solution: 13% (w/v) methacryloylated gelatin-0.25% (w/v) lithium phenyl(2,4,6-trimethylbenzoyl)phosphinate-1000 IU/mL thrombin;
(5) preparation of a component B solution: adding the fibrinogen solution obtained in step (3) to the 10% (w/v) methacryloylated gelatin-0.25% (w/v) lithium phenyl(2,4,6-trimethylbenzoyl)phosphinate precursor solution obtained in step (1), and mixing evenly to obtain the component B solution: 5% (w/v) methacryloylated gelatin-0.125% (w/v) lithium phenyl(2,4,6-trimethylbenzoyl)phosphinate-5% (w/v) fibrinogen;
(6) storage: freeze-drying the obtained component A solution and component B solution each in a volume ratio of 1:1, and storing in a sponge shape;
(7) use method: dissolving a spongy component A and a spongy component B respectively in a solution containing 0.9% sodium chloride in a volume fraction ratio of 1:1 to obtain an injectable solution-like component A and component B. The component A solution and component B solution were put into a duplex syringe in equal volume, and the component A solution and component B solution were injected/sprayed on a bleeding site through a nozzle, and then irradiated with blue light for 10-60 s, which could be converted into a solid hydrogel in situ. In the gel obtained at this time, a volume ratio of fibrin crosslinking to photocrosslinking was 1:1.
(8) a structure of the solid gel as shown in FIG. 3: it was a solid hydrogel composed of both a three-dimensional fibrin network and a three-dimensional photosensitive gel network; and the formed methacryloylated gelatin crosslinked porous structure had a group of the fibrin network inside, and each group of the fibrin network had overall continuity; on the whole, the three-dimensional fibrin network dispersed disorderly throughout a surface and an interior of the solid hydrogel.

Example 2

A mixed solution with a concentration of 10% (w/v) methacryloylated gelatin-0.25% (w/v) lithium phenyl(2,4,6-trimethylbenzoyl)phosphinate-1000 IU/mL thrombin was prepared as a component A solution, and a mixed solution with a concentration of 5% (w/v) methacryloylated gelatin-0.125% (w/v) lithium phenyl(2,4,6-trimethylbenzoyl)phosphinate-5% (w/v) fibrinogen was prepared as a component B solution. The composition, preparation method and use method were generally the same as those in Example 1, except only that a concentration of the methacryloylated gelatin in the component A solution prepared in step (4) was adjusted to 10% (w/v).

Example 3

A mixed solution with a concentration of 8% (w/v) methacryloylated gelatin-0.25% (w/v) lithium phenyl(2,4,6-trimethylbenzoyl)phosphinate-1000 IU/mL thrombin was prepared as a component A solution, and a mixed solution with a concentration of 5% (w/v) methacryloylated gelatin-0.125% (w/v) lithium phenyl(2,4,6-trimethylbenzoyl)phosphinate-5% (w/v) fibrinogen was prepared as a component B solution. The composition, preparation method and use method were generally the same as those in Example 1, except only that a concentration of the methacryloylated gelatin in the component A solution prepared in step (4) was adjusted to 8% (w/v).

Example 4

A mixed solution with a concentration of 5% (w/v) methacryloylated gelatin-0.25% (w/v) lithium phenyl(2,4,6-trimethylbenzoyl)phosphinate-1000 IU/mL thrombin was prepared as a component A solution, and a mixed solution with a concentration of 5% (w/v) methacryloylated gelatin-0.125% (w/v) lithium phenyl(2,4,6-trimethylbenzoyl)phosphinate-5% (w/v) fibrinogen was prepared as a component B solution. The composition, preparation method and use method were generally the same as those in Example 1, except only that a concentration of the methacryloylated gelatin in the component A solution prepared in step (4) was adjusted to 5% (w/v). In the gel obtained at this time, a volume ratio of fibrin crosslinking to photocrosslinking was 2:1.

Example 5

A mixed solution with a concentration of 13% (w/v) methacryloylated gelatin-0.25% (w/v) lithium phenyl(2,4,6-trimethylbenzoyl)phosphinate-1000 IU/mL thrombin was prepared as a component A solution, and a mixed solution with a concentration of 3% (w/v) methacryloylated gelatin-0.125% (w/v) lithium phenyl(2,4,6-trimethylbenzoyl)phosphinate-5% (w/v) fibrinogen was prepared as a component B solution. The composition, preparation method and use method were generally the same as those in Example 1, except only that a concentration of the methacryloylated gelatin in the component B solution prepared in step (5) was adjusted to 3% (w/v).

Example 6

A mixed solution with a concentration of 13% (w/v) methacryloylated gelatin-0.25% (w/v) lithium phenyl(2,4,6-trimethylbenzoyl)phosphinate-500 IU/mL thrombin was prepared as a component A solution, and a mixed solution with a concentration of 5% (w/v) methacryloylated gelatin-0.125% (w/v) lithium phenyl(2,4,6-trimethylbenzoyl)phosphinate-5% (w/v) fibrinogen was prepared as a component B solution. The composition, preparation method and use method were generally the same as those in Example 1, except only that thrombin activity of the component A solution prepared in step (4) was adjusted to 500 IU/mL.

Example 7

A mixed solution with a concentration of 13% (w/v) methacryloylated gelatin-0.25% (w/v) lithium phenyl(2,4,6-trimethylbenzoyl)phosphinate-250 IU/mL thrombin was prepared as a component A solution, and a mixed solution with a concentration of 5% (w/v) methacryloylated gelatin-0.125% (w/v) lithium phenyl(2,4,6-trimethylbenzoyl)phosphinate-5% (w/v) fibrinogen was prepared as a component B solution. The composition, preparation method and use method were generally the same as those in Example 1, except only that thrombin activity of the component A solution prepared in step (4) was adjusted to 250 IU/mL.

Example 8

A mixed solution with a concentration of 13% (w/v) methacryloylated gelatin-0.25% (w/v) lithium phenyl(2,4,6-trimethylbenzoyl)phosphinate-1000 IU/mL thrombin was prepared as a component A solution, and a mixed solution with a concentration of 5% (w/v) methacryloylated gelatin-0.125% (w/v) lithium phenyl(2,4,6-trimethylbenzoyl)phosphinate-3% (w/v) fibrinogen was prepared as a component B solution. The composition, preparation method and use method were generally the same as those in Example 1, except only that a concentration of the fibrinogen in the component B solution prepared in step (5) was adjusted to 3% (w/v). In the gel obtained at this time, a volume ratio of fibrin crosslinking to photocrosslinking was 1:2.

Example 9

A mixed solution with a concentration of 8% (w/v) methacryloylated hyaluronic acid-0.25% (w/v) lithium phenyl(2,4,6-trimethylbenzoyl)phosphinate-1000 IU/mL thrombin was prepared as a component A solution, and a mixed solution with a concentration of 5% (w/v) methacryloylated hyaluronic acid-0.125% (w/v) lithium phenyl(2,4,6-trimethylbenzoyl)phosphinate-5% (w/v) fibrinogen was prepared as a component B solution. The preparation and use methods were generally the same as those in Example 1, except that: (1) a photosensitive material in components A and B of this Example was methacryloylated hyaluronic acid, and a concentration of methacryloylated hyaluronic acid in the component A solution was 8% (w/v); and (2) a preparation process of a methacryloylated hyaluronic acid-lithium phenyl(2,4,6-trimethylbenzoyl)phosphinate precursor solution did not require heating and could be performed at a room temperature. In the gel obtained at this time, a volume ratio of fibrin crosslinking to photocrosslinking was 1:1.

Example 10

A mixed solution with a concentration of 5% (w/v) methacryloylated hyaluronic acid-0.25% (w/v) lithium phenyl(2,4,6-trimethylbenzoyl)phosphinate-1000 IU/mL thrombin was prepared as a component A solution, and a mixed solution with a concentration of 5% (w/v) methacryloylated hyaluronic acid-0.125% (w/v) lithium phenyl(2,4,6-trimethylbenzoyl)phosphinate-5% (w/v) fibrinogen was prepared as a component B solution. The composition, preparation method and use method were generally the same as those in Example 9, except only that a concentration of the methacryloylated hyaluronic acid in the component A solution was adjusted to 5% (w/v).

In the gel obtained at this time, a volume ratio of fibrin crosslinking to photocrosslinking was 2:1.

Example 11

A mixed solution with a concentration of 8% (w/v) methacryloylated hyaluronic acid-0.25% (w/v) lithium phenyl(2,4,6-trimethylbenzoyl)phosphinate-1000 IU/mL thrombin was prepared as a component A solution, and a mixed solution with a concentration of 3% (w/v) methacryloylated hyaluronic acid-0.125% (w/v) lithium phenyl(2,4,6-trimethylbenzoyl)phosphinate-5% (w/v) fibrinogen was prepared as a component B solution. The composition, preparation method and use method were generally the same as those in Example 9, except only that a concentration of the methacryloylated hyaluronic acid in the component B solution was adjusted to 3% (w/v).

Example 12

A mixed solution with a concentration of 8% (w/v) methacryloylated hyaluronic acid-0.25% (w/v) lithium phenyl(2,4,6-trimethylbenzoyl)phosphinate-500 IU/ml thrombin was prepared as a component A solution, and a mixed solution with a concentration of 5% (w/v) methacryloylated hyaluronic acid-0.125% (w/v) lithium phenyl(2,4,6-trimethylbenzoyl)phosphinate-5% (w/v) fibrinogen was prepared as a component B solution. The composition, preparation method and use method were generally the same as those in Example 9, except that thrombin activity of the component A solution was adjusted to 500 IU/mL.

Example 13

A mixed solution with a concentration of 8% (w/v) methacryloylated hyaluronic acid-0.25% (w/v) lithium phenyl(2,4,6-trimethylbenzoyl)phosphinate-1000 IU/mL thrombin was prepared as a component A solution, and a mixed solution with a concentration of 5% (w/v) methacryloylated hyaluronic acid-0.125% (w/v) lithium phenyl(2,4,6-trimethylbenzoyl)phosphinate-3% (w/v) fibrinogen was prepared as a component B solution. The composition, preparation method and use method were generally the same as those in Example 9, except that a concentration of the fibrinogen in the component B solution was adjusted to 3% (w/v). In the gel obtained at this time, a volume ratio of fibrin crosslinking to photocrosslinking was 1:2.

Example 14

A mixed solution with a concentration of 8% (w/v) methacryloylated sodium alginate-0.25% (w/v) lithium phenyl(2,4,6-trimethylbenzoyl)phosphinate-1000 IU/mL thrombin was prepared as a component A solution, and a mixed solution with a concentration of 5% (w/v) methacryloylated sodium alginate-0.125% (w/v) lithium phenyl(2,4,6-trimethylbenzoyl)phosphinate-5% (w/v) fibrinogen was prepared as a component B solution. The preparation method and use method were generally the same as those in Example 9, except only that a photosensitive material in components A and B of this example was methacryloylated sodium alginate. In the gel obtained at this time, a volume ratio of fibrin crosslinking to photocrosslinking was 1:1.

Example 15

A mixed solution with a concentration of 5% (w/v) methacryloylated sodium alginate-0.25% (w/v) lithium phenyl(2,4,6-trimethylbenzoyl)phosphinate-1000 IU/mL thrombin was prepared as a component A solution, and a mixed solution with a concentration of 5% (w/v) methacryloylated sodium alginate-0.125% (w/v) lithium phenyl(2,4,6-trimethylbenzoyl)phosphinate-5% (w/v) fibrinogen was prepared as a component B solution. The composition, preparation method and use method were generally the same as those in Example 14, except only that a concentration of the methacryloylated sodium alginate in the component A solution was adjusted to 5% (w/v). In the gel obtained at this time, a volume ratio of fibrin crosslinking to photocrosslinking was 2:1.

Example 16

A mixed solution with a concentration of 8% (w/v) methacryloylated sodium alginate-0.25% (w/v) lithium phenyl(2,4,6-trimethylbenzoyl)phosphinate-1000 IU/mL thrombin was prepared as a component A solution, and a mixed solution with a concentration of 3% (w/v) methacryloylated sodium alginate-0.125% (w/v) lithium phenyl(2,4,6-trimethylbenzoyl)phosphinate-5% (w/v) fibrinogen was prepared as a component B solution. The composition, preparation method and use method were generally the same as those in Example 14, except only that a concentration of the methacryloylated sodium alginate in the component B solution was adjusted to 3% (w/v).

Example 17

A mixed solution with a concentration of 8% (w/v) methacryloylated sodium alginate-0.25% (w/v) lithium phenyl(2,4,6-trimethylbenzoyl)phosphinate-500 IU/mL thrombin was prepared as a component A solution, and a mixed solution with a concentration of 5% (w/v) methacryloylated sodium alginate-0.125% (w/v) lithium phenyl(2,4,6-trimethylbenzoyl)phosphinate-5% (w/v) fibrinogen was prepared as a component B solution. The composition, preparation method and use method were generally the same as those in Example 14, except that thrombin activity of the component A solution was adjusted to 500 IU/mL.

Example 18

A mixed solution with a concentration of 8% (w/v) methacryloylated sodium alginate-0.25% (w/v) lithium phenyl(2,4,6-trimethylbenzoyl)phosphinate-1000 IU/mL thrombin was prepared as a component A solution, and a mixed solution with a concentration of 5% (w/v) methacryloylated sodium alginate-0.125% (w/v) lithium phenyl(2,4,6-trimethylbenzoyl)phosphinate-3% (w/v) fibrinogen was prepared as a component B solution. The composition, preparation method and use method were generally the same as those in Example 14, except that a concentration of the fibrinogen in the component B solution was adjusted to 3% (w/v). In the gel obtained at this time, a volume ratio of fibrin crosslinking to photocrosslinking was 1:2.

Example 19

A mixed solution with a concentration of 10% (w/v) methacryloylated silk fibroin-0.25% (w/v) lithium phenyl(2,4,6-trimethylbenzoyl)phosphinate-1000 IU/mL thrombin was prepared as a component A solution, and a mixed solution with a concentration of 5% (w/v) methacryloylated silk fibroin-0.125% (w/v) lithium phenyl(2,4,6-trimethylbenzoyl)phosphinate-5% (w/v) fibrinogen was prepared as a component B solution. The preparation method and use method were generally the same as those in Example 9, except only that a photosensitive material in components A and B of this example was methacryloylated silk fibroin, and a concentration of the methacryloylated silk fibroin in the component A solution was 10% (w/v). In the gel obtained at this time, a volume ratio of fibrin crosslinking to photocrosslinking was 1:1.

Example 20

A mixed solution with a concentration of 8% (w/v) methacryloylated silk fibroin-0.25% (w/v) lithium phenyl(2,4,6-trimethylbenzoyl)phosphinate-1000 IU/mL thrombin was prepared as a component A solution, and a mixed solution with a phenyl(2,4,6-trimethylbenzoyl)phosphinate-5% (w/v) fibrinogen was prepared as a component B solution. The composition, preparation method and use method were generally the same as those in Example 19, except only that a concentration of the methacryloylated silk fibroin in the component A solution was adjusted to 8% (w/v).

Example 21

A mixed solution with a concentration of 5% (w/v) methacryloylated silk fibroin-0.25% (w/v) lithium phenyl(2,4,6-trimethylbenzoyl)phosphinate-1000 IU/mL thrombin was prepared as a component A solution, and a mixed solution with a concentration of 5% (w/v) methacryloylated silk fibroin-0.125% (w/v) lithium phenyl(2,4,6-trimethylbenzoyl)phosphinate-5% (w/v) fibrinogen was prepared as a component B solution. The composition, preparation method and use method were generally the same as those in Example 19, except only that a concentration of the methacryloylated silk fibroin in the component A solution was adjusted to 5% (w/v). In the gel obtained at this time, a volume ratio of fibrin crosslinking to photocrosslinking was 2:1.

Example 22

A mixed solution with a concentration of 10% (w/v) methacryloylated silk fibroin-0.25% (w/v) lithium phenyl(2,4,6-trimethylbenzoyl)phosphinate-1000 IU/mL thrombin was prepared as a component A solution, and a mixed solution with a concentration of 3% (w/v) methacryloylated silk fibroin-0.125% (w/v) lithium phenyl(2,4,6-trimethylbenzoyl)phosphinate-5% (w/v) fibrinogen was prepared as a component B solution. The composition, preparation method and use method were generally the same as those in Example 19, except only that a concentration of the methacryloylated silk fibroin in the component B solution was adjusted to 3% (w/v).

Example 23

A mixed solution with a concentration of 10% (w/v) methacryloylated silk fibroin-0.25% (w/v) lithium phenyl(2,4,6-trimethylbenzoyl)phosphinate-500 IU/mL thrombin was prepared as a component A solution, and a mixed solution with a phenyl(2,4,6-trimethylbenzoyl)phosphinate-5% (w/v) fibrinogen was prepared as a component B solution. The composition, preparation method and use method were generally the same as those in Example 19, except that thrombin activity of the component A solution was adjusted to 500 IU/mL.

Example 24

A mixed solution with a concentration of 10% (w/v) methacryloylated silk fibroin-0.25% (w/v) lithium phenyl(2,4,6-trimethylbenzoyl)phosphinate-1000 IU/mL thrombin was prepared as a component A solution, and a mixed solution with a concentration of 5% (w/v) methacryloylated silk fibroin-0.125% (w/v) lithium phenyl(2,4,6-trimethylbenzoyl)phosphinate-3% (w/v) fibrinogen was prepared as a component B solution. The composition, preparation method and use method were generally the same as those in Example 19, except that a concentration of the fibrinogen in the component B solution was adjusted to 3% (w/v). In the gel obtained at this time, a volume ratio of fibrin crosslinking to photocrosslinking was 1:2.

Example 25

A mixed solution with a concentration of 3% (w/v) methacryloylated chitosan-0.1% (w/v) lithium phenyl(2,4,6-trimethylbenzoyl)phosphinate-1000 IU/mL thrombin was prepared as a component A solution, and a mixed solution with a concentration of 1% (w/v) methacryloylated chitosan-0.1% (w/v) lithium phenyl(2,4,6-trimethylbenzoyl)phosphinate-5% (w/v) fibrinogen was prepared as a component B solution. The preparation method and use method were generally the same as those in Example 9, except that a photosensitive material in components A and B of this example was methacryloylated chitosan, and a concentration of the methacryloylated chitosan in the component A solution was 3% (w/v), and a concentration of the methacryloylated chitosan in the component B solution was 1% (w/v). In the gel obtained at this time, a volume ratio of fibrin crosslinking to photocrosslinking was 1:1.

Example 26

A mixed solution with a concentration of 2% (w/v) methacryloylated chitosan-0.1% (w/v) lithium phenyl(2,4,6-trimethylbenzoyl)phosphinate-1000 IU/mL thrombin was prepared as a component A solution, and a mixed solution with a concentration of 1% (w/v) methacryloylated chitosan-0.1% (w/v) lithium phenyl(2,4,6-trimethylbenzoyl)phosphinate-5% (w/v) fibrinogen was prepared as a component B solution. The composition, preparation method and use method were generally the same as those in Example 25, except only that a concentration of the methacryloylated chitosan in the component A solution was adjusted to 2% (w/v).

Example 27

A mixed solution with a concentration of 1% (w/v) methacryloylated chitosan-0.1% (w/v) lithium phenyl(2,4,6-trimethylbenzoyl)phosphinate-1000 IU/mL thrombin was prepared as a component A solution, and a mixed solution with a concentration of 1% (w/v) methacryloylated chitosan-0.1% (w/v) lithium phenyl(2,4,6-trimethylbenzoyl)phosphinate-5% (w/v) fibrinogen was prepared as a component B solution. The composition, preparation method and use method were generally the same as those in Example 25, except only that a concentration of the methacryloylated chitosan in the component A solution was adjusted to 1% (w/v). In the gel obtained at this time, a volume ratio of fibrin crosslinking to photocrosslinking was 2:1.

Example 28

A mixed solution with a concentration of 3% (w/v) methacryloylated chitosan-0.1% (w/v) lithium phenyl(2,4,6-trimethylbenzoyl)phosphinate-1000 IU/mL thrombin was prepared as a component A solution, and a mixed solution with a concentration of 0.5% (w/v) methacryloylated chitosan-0.1% (w/v) lithium phenyl(2,4,6-trimethylbenzoyl)phosphinate-5% (w/v) fibrinogen was prepared as a component B solution. The composition, preparation method and use method were generally the same as those in Example 25, except only that a concentration of the methacryloylated chitosan in the component B solution was adjusted to 0.5% (w/v).

Example 29

A mixed solution with a concentration of 3% (w/v) methacryloylated chitosan-0.1% (w/v) lithium phenyl(2,4,6-trimethylbenzoyl)phosphinate-500 IU/mL thrombin was prepared as a component A solution, and a mixed solution with a concentration of 1% (w/v) methacryloylated chitosan-0.1% (w/v) lithium phenyl(2,4,6-trimethylbenzoyl)phosphinate-5% (w/v) fibrinogen was prepared as a component B solution. The composition, preparation method and use method were generally the same as those in Example 25, except that thrombin activity of the component A solution was adjusted to 500 IU/mL.

Example 30

A mixed solution with a concentration of 3% (w/v) methacryloylated chitosan-0.1% (w/v) lithium phenyl(2,4,6-trimethylbenzoyl)phosphinate-1000 IU/mL thrombin was prepared as a component A solution, and a mixed solution with a concentration of 1% (w/v) methacryloylated chitosan- 0.1% (w/v) lithium phenyl(2,4,6-trimethylbenzoyl)phosphinate-3% (w/v) fibrinogen was prepared as a component B solution. The composition, preparation method and use method were generally the same as those in Example 25, except that a concentration of the fibrinogen in the component B solution was adjusted to 3% (w/v). In the gel obtained at this time, a volume ratio of fibrin crosslinking to photocrosslinking was 1:2.

Example 31

A mixed solution with a concentration of 20% (w/v) polyether F127 diacrylate-0.25% (w/v) lithium phenyl(2,4,6-trimethylbenzoyl)phosphinate-1000 IU/mL thrombin was prepared as a component A solution, and a mixed solution with a concentration of 10% (w/v) polyether F127 diacrylate-0.25% (w/v) lithium phenyl(2,4,6-trimethylbenzoyl) phosphinate-5% (w/v) fibrinogen was prepared as a component B solution. The preparation method and use method were generally the same as those in Example 9, except that a photosensitive material in components A and B of this example was polyether F127 diacrylate, and a concentration of the polyether F127 diacrylate in the component A solution was 20% (w/v), and a concentration of the polyether F127 diacrylate in the component B solution was 10% (w/v). In the gel obtained at this time, the volume ratio of fibrin crosslinking to photocrosslinking was 1:1.

Example 32

A mixed solution with a concentration of 15% (w/v) polyether F127 diacrylate-0.25% (w/v) lithium phenyl(2,4,6-trimethylbenzoyl)phosphinate-1000 IU/mL thrombin was prepared as a component A solution, and a mixed solution with a concentration of 10% (w/v) polyether F127 diacrylate-0.25% (w/v) lithium phenyl(2,4,6-trimethylbenzoyl) phosphinate-5% (w/v) fibrinogen was prepared as a component B solution. The composition, preparation method and use method were generally the same as those in Example 31, except that a concentration of the polyether F127 diacrylate in the component A solution was adjusted to 15% (w/v).

Example 33

A mixed solution with a concentration of 10% (w/v) polyether F127 diacrylate-0.25% (w/v) lithium phenyl(2,4,6-trimethylbenzoyl)phosphinate-1000 IU/mL thrombin was prepared as a component A solution, and a mixed solution with a concentration of 10% (w/v) polyether F127 diacrylate-0.25% (w/v) lithium phenyl(2,4,6-trimethylbenzoyl) phosphinate-5% (w/v) fibrinogen was prepared as a component B solution. The composition, preparation method and use method were generally the same as those in Example 31, except that a concentration of the polyether F127 diacrylate in the component A solution was adjusted to 10% (w/v). In the gel obtained at this time, a volume ratio of fibrin crosslinking to photocrosslinking was 2:1.

Example 34

A mixed solution with a concentration of 20% (w/v) polyether F127 diacrylate-0.25% (w/v) lithium phenyl(2,4,6-trimethylbenzoyl)phosphinate-1000 IU/mL thrombin was prepared as a component A solution, and a mixed solution with a concentration of 5% (w/v) polyether F127 diacrylate-0.25% (w/v) lithium phenyl(2,4,6-trimethylbenzoyl)phosphinate-5% (w/v) fibrinogen was prepared as a component B solution. The composition, preparation method and use method were generally the same as those in Example 31, except that a concentration of the polyether F127 diacrylate in the component B solution was adjusted to 5% (w/v).

Example 35

A mixed solution with a concentration of 20% (w/v) polyether F127 diacrylate-0.25% (w/v) lithium phenyl(2,4,6-trimethylbenzoyl)phosphinate-500 IU/mL thrombin was prepared as a component A solution, and a mixed solution with a concentration of 10% (w/v) polyether F127 diacrylate-0.25% (w/v) lithium phenyl(2,4,6-trimethylbenzoyl) phosphinate-5% (w/v) fibrinogen was prepared as a component B solution. The composition, preparation method and use method were generally the same as those in Example 31, except that thrombin activity of the component A solution was adjusted to 500 IU/mL.

Example 36

A mixed solution with a concentration of 20% (w/v) polyether F127 diacrylate-0.25% (w/v) lithium phenyl(2,4,6-trimethylbenzoyl)phosphinate-1000 IU/mL thrombin was prepared as a component A solution, and a mixed solution with a concentration of 10% (w/v) polyether F127 diacrylate-0.25% (w/v) lithium phenyl(2,4,6-trimethylbenzoyl) phosphinate-3% (w/v) fibrinogen was prepared as a component B solution. The composition, preparation method and use method were generally the same as those in Example 31, except that a concentration of the fibrinogen in the component B solution was adjusted to 3% (w/v). In the gel obtained at this time, a volume ratio of fibrin crosslinking to photocrosslinking was 1:2.

Comparative Example 1

Figures 1, 2:
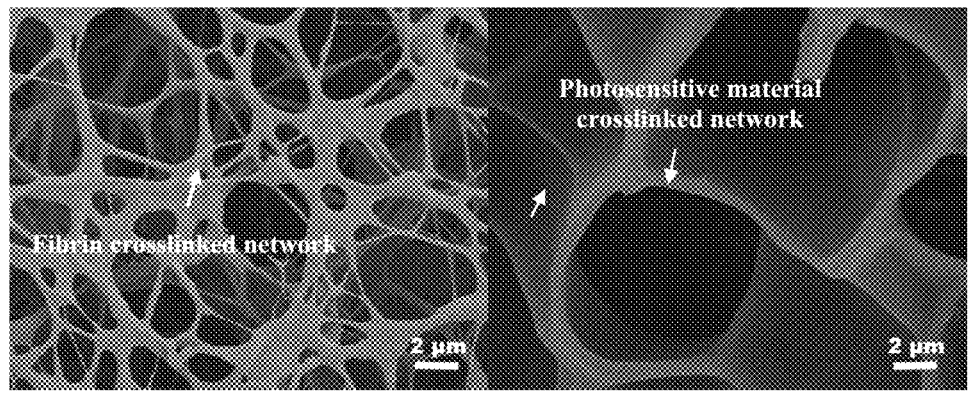
FIG. 1 is an SEM image of fibrin crosslinking in Comparative example 1.
FIG. 2 is an SEM image of methacryloylated gelatin photocrosslinking in a precursor solution in Comparative example 2.

A freeze-dried fibrin adhesive for external use (Hugulaishi, purchased from Shanghai RAAS) includes an enzyme reagent and a fibrinogen reagent. The enzyme reagent and the fibrinogen reagent were prepared into solutions according to their instructions, and enzymatic crosslinking was completed about 1 s after mixing to obtain a fibrin adhesive. A microstructure of the adhesive is shown in FIG. 1.

Comparative Example 2

A preparation method of a 9% (w/v) methacryloylated gelatin-0.25% (w/v) lithium phenyl(2,4,6-trimethylbenzoyl) phosphinate precursor solution was generally the same as that of the component A solution in Example 2, except only that thrombin was not added to the solution.

Comparative Example 3

Components and a preparation method of a 13% (w/v) methacryloylated gelatin-0.25% (w/v) lithium phenyl(2,4,6-trimethylbenzoyl)phosphinate-1000 IU/mL thrombin mixed solution were the same as those of the component A solution in Example 2.

Comparative Example 4

Components and a preparation method of a 5% (w/v) methacryloylated gelatin-0.125% (w/v) lithium phenyl(2,4, 6-trimethylbenzoyl)phosphinate-5% (w/v) fibrinogen mixed solution were the same as step (5) in Example 1.

Comparative Example 5

A mixed solution with a concentration of 30% (w/v) methacryloylated sericin-0.5% (w/v) lithium phenyl(2,4,6-trimethylbenzoyl)phosphinate-1000 IU/mL thrombin was prepared as a component A solution, and a mixed solution with a concentration of 20% (w/v) methacryloylated sericin-0.5% (w/v) lithium phenyl(2,4,6-trimethylbenzoyl)phosphinate-5% (w/v) fibrinogen was prepared as a component B solution. The preparation method was generally the same as that in Example 9, except that a photosensitive material in components A and B in this comparative example was methacryloylated sericin, and a concentration of the methacryloylated sericin was 30% (w/v), and a concentration of the lithium phenyl(2,4,6-trimethylbenzoyl)phosphinate was 0.5% (w/v) in the component A solution, and a concentration of the methacryloylated sericin was 20% (w/v), and a concentration of the lithium phenyl(2,4,6-trimethylbenzoyl)phosphinate was 0.5% (w/v) in the component B solution. In the gel obtained at this time, a volume ratio of fibrin crosslinking to photocrosslinking was 1:1.

Comparative Example 6

A mixed solution with a concentration of 10% (w/v) methacryloylated glucan-0.25% (w/v) lithium phenyl(2,4,6-trimethylbenzoyl)phosphinate-1000 IU/mL thrombin was prepared as a component A solution, and a mixed solution with a concentration of 10% (w/v) methacryloylated glucan-0.125% (w/v) lithium phenyl(2,4,6-trimethylbenzoyl)phosphinate-5% (w/v) fibrinogen was prepared as a component B solution. The preparation method was generally the same as that in Example 9, except that a photosensitive material in components A and B of this comparative example was methacryloylated glucan, and a concentration of the methacryloylated glucan in the component A solution was 10% (w/v), and a concentration of the methacryloylated glucan in the component B solution was 5% (w/v). In the gel obtained at this time, a volume ratio of fibrin crosslinking to photocrosslinking was 1:1.

Performance Test

In order to verify the performance of the double-crosslinked fibrin gels obtained from Examples 1-36 and the hydrogels from Comparative examples 1-6, they were tested by the following gelation time performance test, adhesion strength test and animal hemostasis experiment, respectively.
Gelation Time Test
Detection Object:
The aforementioned Examples 1-36 and Comparative examples 1-6;
Detection Method:
Rheological analysis was conducted on Examples 1-36 and Comparative examples 1-6 to compare their gelation time. Results are shown in Table 1. Specific operation method: a dynamic rheological experiment was performed at 37° C. using an HAAKE RS6000 optical rheometer with parallel plate (P20 TIL, 20-mm diameter) geometry. The time scanning oscillation test of Examples 1-36 and Comparative examples 1-6 hydrogels was performed for 300 seconds under 5% strain and a frequency of 1 Hz. Strain scanning was performed on a pre-gel solution to verify a linear response. A gel point was determined when a torsional modulus (G') exceeded a loss modulus (G").

Adhesion Strength Test
The aforementioned Examples 1-36 and Comparative examples 1-6;
Detection Method:
Specific operation: the pig skin was cut into a 40 mm×20 mm rectangle, the two pieces of pig skin were bonded with 500 µl of Examples 1-36 and Comparative examples 1-6, and a mixed solution of components A and B in Examples 1-36 and a precursor solution in Comparative examples 2-6 were illuminated with blue light of the same wave band for 60 s. Afterwards, adhesion strength was tested at a strain rate of 1 mm/min. A microstructure of the gel formed after photocrosslinking of the precursor solution in Comparative example 2 is shown in FIG. 2; and a microstructure of the gel formed after photocrosslinking of the mixed solution in Example 1 is shown in FIG. 3. The reading at the time the gel fell off the pig skin was recorded, which was the adhesion strength (Kpa). Test results are shown in Table 1.
Hemostatic Effect Test
Detection Object:
Example 1, Example 9, Example 14, Example 19, Example 25, and Example 31, and Comparative examples 1-6 in the present invention;
Detection Method:
One-cm incision bleeding model in a rabbit liver surface: New Zealand white rabbits were anesthetized, with the abdomen exposed, fixed on the operating table and incised in the middle of the abdomen, the liver was exposed, and a 1 cm*0.5 cm bleeding model was made on the liver; the weighed filter paper, the mixed solution obtained by injecting the components A and B of Examples 1, 9, 14, 19, 25, and 31 according to the injection method described in step (7) of Example 1, and the precursor solution in Comparative examples 1-6 were used as hemostatic materials to cover the bleeding site (where each example and Comparative examples 2-6 of the present invention were illuminated with blue light of the same wave band while covering the bleeding site) until the bleeding stopped, and the bleeding time and blood loss were recorded. Results are shown in Table 1, FIG. 4, and FIG. 5.

TABLE 1

| Example | Gelation time (s) | Adhesion strength (kPa) | Hemostasis time (s) | Blood loss (mg) |
| --- | --- | --- | --- | --- |
| Example 1 | 2 | 106 | 6 ± 2 | 12 ± 6 |
| Example 2 | 2 | 96 | — | — |
| Example 3 | 1 | 88 | — | — |
| Example 4 | 1 | 82 | — | — |
| Example 5 | 1 | 89 | — | — |
| Example 6 | 2 | 97 | — | — |
| Example 7 | 2 | 100 | — | — |
| Example 8 | 2 | 103 | — | — |
| Example 9 | 2 | 98 | 12 ± 5 | 24 ± 7 |
| Example 10 | 1 | 87 | — | — |
| Example 11 | 2 | 91 | — | — |
| Example 12 | 2 | 96 | — | — |
| Example 13 | 3 | 97 | — | — |
| Example 14 | 2 | 96 | 20 ± 5 | 35 ± 6 |
| Example 15 | 1 | 87 | — | — |
| Example 16 | 2 | 90 | — | — |
| Example 17 | 3 | 93 | — | — |
| Example 18 | 3 | 95 | — | — |
| Example 19 | 2 | 105 | 15 ± 4 | 23 ± 7 |
| Example 20 | 2 | 95 | — | — |
| Example 21 | 1 | 87 | — | — |
| Example 22 | 2 | 94 | — | — |
| Example 23 | 3 | 101 | — | — |
| Example 24 | 3 | 102 | — | — |
| Example 25 | 2 | 99 | 22 ± 6 | 37 ± 6 |

TABLE 1-continued

| Example | Gelation time (s) | Adhesion strength (kPa) | Hemostasis time (s) | Blood loss (mg) |
|---|---|---|---|---|
| Example 26 | 2 | 93 | — | — |
| Example 27 | 1 | 86 | — | — |
| Example 28 | 2 | 89 | — | — |
| Example 29 | 3 | 93 | — | — |
| Example 30 | 3 | 95 | — | — |
| Example 31 | 2 | 132 | 22 ± 8 | 21 ± 10 |
| Example 32 | 2 | 122 | — | — |
| Example 33 | 1 | 108 | — | — |
| Example 34 | 2 | 112 | — | — |
| Example 35 | 3 | 123 | — | — |
| Example 36 | 3 | 129 | — | — |
| Comparative example 1 | 1 | 6 | 72 ± 5 | 139 ± 23 |
| Comparative example 2 | 8 | 80 | 53 ± 5 | 96 ± 8 |
| Comparative example 3 | 9 | 76 | 48 ± 4 | 91 ± 6 |
| Comparative example 4 | 14 | 70 | 60 ± 7 | 109 ± 12 |
| Comparative example 5 | 3 | 29 | 54 ± 6 | 104 ± 7 |
| Comparative example 6 | 2 | 45 | 49 ± 6 | 96 ± 8 |

The values of hemostasis time and blood loss were expressed as (mean ± standard deviation).

DESCRIPTION

Result Analysis:

As could be seen from FIG. 1, in the fibrin glue adhesive of Comparative example 1, only fibrin was crosslinked to present a network structure. As could be seen from FIG. 2, only the methacryloylated gelatin was photocrosslinked to present a porous structure after illumination of the precursor solution of Comparative example 2. As could be seen from FIG. 3, the mixed solution of the components A and B of Example 1 in the present invention could have both a fibrin crosslinked network structure and a methacryloylated gelatin crosslinked porous structure after illumination, and the channels of the formed methacryloylated gelatin crosslinked porous structure were all distributed with an integral and continuous three-dimensional fibrin network structure.

As could be seen from Table 1, the gelation time range of Examples 1-36 was 1-3 s, and the gelation time would be prolonged with the increase of a photocrosslinking ratio when the photosensitive materials were the same, but the gelation time of all types of photosensitive materials selected in Examples 1-36 at a specific double-crosslinking ratio was significantly lower than that in Comparative examples 2-4 (the gelation time of Comparative example 2 was 8 s, the gelation time of Comparative example 3 was 9 s, and the gelation time of Comparative example 4 was 14 s).

As could be seen from Table 1, the adhesion strength range of Examples 1-36 was 82-132 kPa, and the adhesion strength of the gel decreased with the decrease of a photosensitive material concentration when the photosensitive materials were the same, but the adhesion strength of all types of photosensitive materials selected in Examples 1-36 at a specific double-crosslinking ratio was higher than that in each comparative example (the adhesion strength of Comparative example 1 was 6 kPa, the adhesion strength of Comparative example 2 was 80 kPa, the adhesion strength of Comparative example 3 was 76 kPa, the adhesion strength of Comparative example 4 was 70 kPa, the adhesion strength of Comparative example 5 was 29 kPa, and the adhesion strength of Comparative example 6 was 45 kPa).

Figure 4:
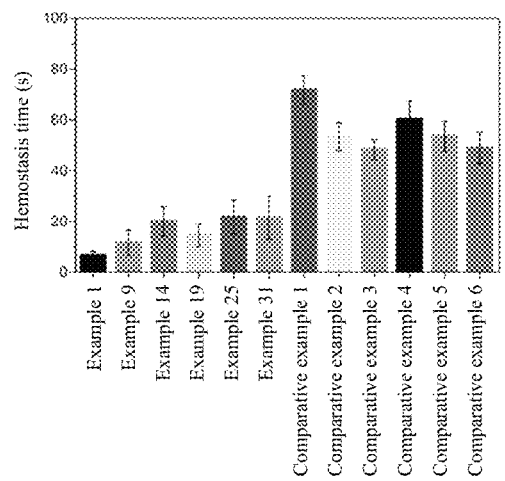
FIG. 4 illustrates comparison of hemostasis time between Examples 1, 9, 14, 19, 25, and 31, and Comparative examples 1-6.
Figure 5:
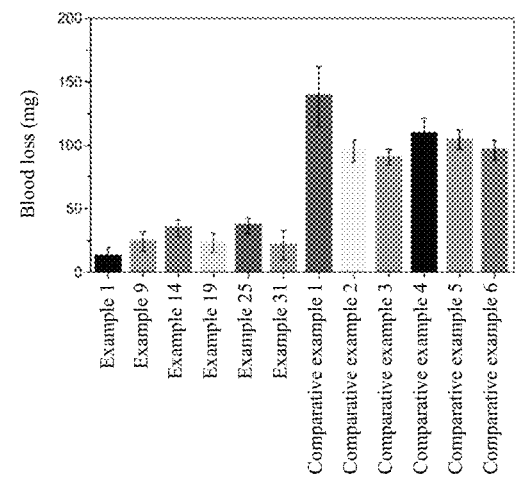
FIG. 5 illustrates comparison of blood loss between Examples 1, 9, 14, 19, 25, and 31, and the Comparative examples 1-6.

As could be seen from Table 1, FIG. 4, and FIG. 5, the hemostasis time of Example 1, Example 9, Example 14, Example 19, Example 25, and Example 31 was 6 s-24 s, which was significantly lower than the hemostasis time of more than 40 s of Comparative examples 1-6. The average blood loss of Example 1, Example 9, Example 14, Example 19, Example 25, and Example 31 was 12 mg-37 mg, which was significantly lower than the blood loss of more than 90 mg of Comparative examples 1-6.

In short, when the double-crosslinked fibrin gel of the present invention was applied to a bleeding wound, a fibrin clot could be formed immediately (about 1 s), which played a "preliminary" role in blocking the wound and blocked the outflow of blood; at the same time, the enzyme in the fibrin clot converted the fibrinogen in the blood into a clot, which had an efficient procoagulant effect; and furthermore, the photosensitive material formed a photosensitive gel under light excitation, which had strong wet tissue adhesion and exhibited a "strong" wound blocking effect. The interaction between fibrin crosslinked and photocrosslinked structures had both preliminary wound blocking and strong tissue adhesion functions, thereby achieving excellent hemostatic effects.

The above provides a detailed introduction to the specific embodiments of the present invention. It should be understood that the present invention is not limited to specific implementations, and any variations, modifications, equivalent substitutions, or improvements made within the spirit and principles of the present invention do not affect the substantive content of the present invention, and should be included in the scope of protection of the claims of the present invention.

The invention claimed is:

1. A raw material composition for preparing a double-crosslinked fibrin adhesive for rapid hemostasis in a bleeding wound in situ by mixing, comprising: a composition A and a composition B,
wherein in parts by weight,
the composition A comprises 10-200 parts of a photosensitive material, 1-3 parts of a photoinitiator, 0.14-0.28 parts of an enzyme, and 1.11-8.88 parts of a water-soluble inorganic calcium salt, and
the composition B comprises 5-100 parts of the photosensitive material, 1-2 parts of the photoinitiator and 30-50 parts of fibrinogen,
a mass ratio of the composition A to the composition B is 1.4:10-14:1,
the photosensitive material is a methacryloylated polymer or a derivative thereof, a polyacrylate polymer or a derivative thereof, or a composite system comprising the methacryloylated polymer or the polyacrylate polymer,
wherein the methacryloylated polymer or the derivative thereof is at least one polymer selected from the group consisting of methacryloylated gelatin or a derivative thereof, methacryloylated hyaluronic acid or a derivative thereof, methacryloylated sodium alginate or a derivative thereof, methacryloylated silk fibroin or a derivative thereof, methacryloylated chitosan or a derivative thereof, and methacryloylated carboxymethyl chitosan or a derivative thereof,
the enzyme is at least one enzyme selected from the group consisting of human thrombin, recombinant human thrombin, bovine thrombin, porcine thrombin, and hemocoagulase, wherein the double-crosslinked fibrin adhesive is a solid hydrogel composed of a three-dimensional fibrin network and a three-dimensional photosensitive gel network, each channel of the photosensitive gel network has a group of the fibrin network inside, and each group of the fibrin network has overall continuity, and on the whole, the three-dimensional fibrin network disperses disorderly throughout a surface and an interior of the solid hydrogel.

2. The raw material composition according to claim 1, wherein parts by weight of the photosensitive material in the composition A are greater than parts by weight of the photosensitive material in the composition B.

3. The raw material composition according to claim 1, wherein the mass ratio of the composition A to the composition B is 1.4:1-1.4:10.

4. The raw material composition according to claim 1, wherein, in parts by weight,
the composition A comprises 80-200 parts of the photosensitive material, 1-3 parts of the photoinitiator, 0.14-0.28 parts of the enzyme, and 1.11-8.88 parts of the water-soluble inorganic calcium salt, and
the composition B comprises 30-100 parts of the photosensitive material, 1-2 parts of the photoinitiator, and 30-50 parts of the fibrinogen.

5. The raw material composition according to claim 1, wherein the polyacrylate polymer or the derivative thereof is selected from the group consisting of polyether diacrylate or a derivative thereof and polyethylene glycol diacrylate or a derivative thereof.

6. The raw material composition according to claim 1, wherein the composite system comprising the methacryloylated polymer is selected from the group consisting of a methacryloylated gelatin-polyvinyl alcohol system, a methacryloylated gelatin-polyurethane system, a methacryloylated gelatin-polylactic acid system, a methacryloylated gelatin-cellulose system, a methacryloylated hyaluronic acid-polyvinyl alcohol system, a methacryloylated hyaluronic acid-polyurethane system, a methacryloylated hyaluronic acid-polylactic acid system, a methacryloylated hyaluronic acid-cellulose system, a methacryloylated sodium alginate-polyvinyl alcohol system, a methacryloylated sodium alginate-polyurethane system, a methacryloylated sodium alginate-polylactic acid system, a methacryloylated sodium alginate-cellulose system, a methacryloylated silk fibroin-polyvinyl alcohol system, a methacryloylated silk fibroin-polyurethane system, a methacryloylated silk fibroin-polylactic acid system, a methacryloylated silk fibroin-cellulose system, a methacryloylated chitosan-polyvinyl alcohol system, a methacryloylated chitosan-polyurethane system, a methacryloylated chitosan-polylactic acid system, a methacryloylated chitosan-cellulose system, a methacryloylated carboxymethyl chitosan-polyvinyl alcohol system, a methacryloylated carboxymethyl chitosan-polyurethane system, a methacryloylated carboxymethyl chitosan-polylactic acid system, and a methacryloylated carboxymethyl chitosan-cellulose system.

7. The raw material composition according to claim 1, wherein the photosensitive material is methacryloylated gelatin or a derivative thereof, or methacryloylated silk fibroin or a derivative thereof.

8. The raw material composition according to claim 1, wherein the photoinitiator is at least one material selected from the group consisting of lithium phenyl (2,4,6-trimethylbenzoyl)phosphinate, 2-hydroxyl-4'-(2-hydroxyethoxy)-2-methylpropiophenone, ethyl (2,4,6-trimethylbenzoyl)phenylphosphinate, 2-methyl-1-[4-methylthiophenyl]-2-morpholino-1-propanone, methyl ortho-benzoylbenzoate, 2-Benzyl-2-(dimethylamino)-4'-morpholinobutyrophenone, and 2,2-azo (2-methyl-N-(2-hydroxylethyl) propionamide).

9. The raw material composition according to claim 1, wherein the fibrinogen is at least one fibrinogen selected from the group consisting of human fibrinogen, bovine fibrinogen, and porcine fibrinogen.

10. The raw material composition according to claim 1, wherein the water-soluble inorganic calcium salt is calcium chloride, calcium nitrate, or calcium sulfate.

11. The raw material composition according to claim 1, wherein the raw material composition is a freeze-dried powder, an injection, a sponge, or a granule.

12. A method of preparing the raw material composition according to claim 1, comprising:
mixing a photosensitive material and a photoinitiator dissolved in a solvent so as to obtain a mixed solution;
mixing the mixed solution with a solution containing thrombin and a calcium ion so as to obtain a first precursor solution, which has a concentration ratio of the photosensitive material, the photoinitiator, the enzyme, and the calcium ion of 10-200:1-3:0.14-0.28: 1.11-8.88,
wherein a storage time of the first precursor solution in a room temperature environment is limited to be less than 30 minutes;
mixing the mixed solution with a solution containing fibrinogen to obtain a second precursor solution, which has a concentration ratio of the photosensitive material, the photoinitiator and the fibrinogen in the second precursor solution of 5-100:1-2:30-50; and
mixing the first precursor solution and the second precursor solution so as to obtain a liquid raw material composition,
wherein the photosensitive material is a methacryloylated polymer or a derivative thereof, a polyacrylate polymer or a derivative thereof, or a composite system comprising the methacryloylated polymer or the polyacrylate polymer; and
the methacryloylated polymer or the derivative thereof is at least one material selected from the group consisting of:
methacryloylated gelatin or a derivative thereof, methacryloylated hyaluronic acid or a derivative thereof, methacryloylated sodium alginate or a derivative thereof, methacryloylated silk fibroin or a derivative thereof, methacryloylated chitosan or a derivative thereof, and methacryloylated carboxymethyl chitosan or a derivative thereof.

13. The method according to claim 12, further comprising freeze-drying of the liquid raw material composition so as to obtain a solid raw material composition, wherein the solid raw material composition is in a form of a freeze-dried powder, a sponge or a granule.

14. The method according to claim 12, wherein a concentration of the photosensitive material in the first precursor solution is greater than 0.5% (w/v), and a concentration of the photosensitive material in the second precursor solution is lower than the concentration of the photosensitive material in the first precursor solution.

15. The method according to claim 12,
wherein the mixing a photosensitive material and a photoinitiator dissolved in a solvent so as to obtain a mixed solution comprises:
1) preparing a first mixed solution of the photosensitive material and the photoinitiator dissolved in the solvent that has a concentration ratio of the photosensitive material and the photoinitiator at 10-200:1-3 and a concentration of the photosensitive material at 0.5%-30% (w/v); and 2) preparing a second mixed solution of the photosensitive material and the photoinitiator dissolved in the solvent that has a concentration ratio of the photosensitive material and the photoinitiator at 5-100:1-2 and a concentration of the photosensitive material to be lower than that in the first mixed solution, wherein the mixing the mixed solution with a solution containing thrombin and a calcium ion so as to obtain a first precursor solution comprises:

3) mixing the first mixed solution with the solution containing the enzyme and the calcium ion to obtain the first precursor solution, and wherein the mixing the mixed solution with a solution containing fibrinogen to obtain the second precursor solution comprises:

4) mixing the second mixed solution with the solution containing the fibrinogen to obtain the second precursor solution.

16. The method according to claim 12, wherein the solution containing the enzyme and the calcium ion is prepared by adding a solvent and a water-soluble inorganic calcium salt solution to the enzyme and completely dissolving, so as to obtain an enzyme solution containing $Ca^{2+}$, in which the enzyme activity is 500 IU-2000 IU/ml and a $Ca^{2+}$ concentration is 60-100 mmol/L.

17. The method according to claim 12, wherein a concentration of the fibrinogen in the solution containing the fibrinogen is 5%-10% (w/v).

18. The method according to claim 12, wherein the concentration of the photosensitive material in the first precursor solution is 1%-30% (w/v).

19. The method according to claim 12, wherein enzyme activity in the first precursor solution is not less than 200 IU/ml.

20. The method according to claim 12, wherein a concentration of the calcium ion in the first precursor solution is not less than 20 mmol/L.

21. The method according to claim 12, wherein the concentration of the photosensitive material in the second precursor solution is 1%-10% (w/v) and not higher than the concentration of the photosensitive material in the first precursor solution.

22. The method according to claim 12, wherein a concentration of the fibrinogen in the second precursor solution is not less than 3% (w/v).

* * * * *